United States Patent [19]

Torossian et al.

[11] 4,269,778

[45] May 26, 1981

[54] PROCESS FOR THE PREPARATION OF STEROIDS

[75] Inventors: Diéran R. Torossian, Bourg-La-Reine; Gilbert G. Aubard, Palaiseau, both of France

[73] Assignee: SIPSY, Avrille, France

[21] Appl. No.: 96,153

[22] Filed: Nov. 20, 1979

[30] Foreign Application Priority Data

Dec. 1, 1978 [FR] France ................................. 78 33959

[51] Int. Cl.$^3$ ............................................... C07J 5/00
[52] U.S. Cl. ............................................... 260/397.45
[58] Field of Search ................................. 260/397.45; /Steroids MS File

[56] References Cited

U.S. PATENT DOCUMENTS 3,803,133   4/1974   Vogt ........................... 260/239.55 D Primary Examiner—Elbert L. Roberts
Attorney, Agent, or Firm—Cushman, Darby & Cushman

[57] ABSTRACT

Process for the preparation of steroids.

The steroid 21-thioesters are prepared by preparing the corresponding sulphonates in acetonic suspension and by reacting this suspension directly with a thiocarboxylate.

Preparation of synthesis intermediates.

10 Claims, No Drawings

PROCESS FOR THE PREPARATION OF STEROIDS

The present invention is concerned with steroids and, more especially with industrial processes for the preparation of intermediate steroids useful in the preparation of pharmacologically active compounds.

It is known to prepare a steroid of formula: A—CH$_2$—S—CO—R in which R is alkyl, cycloalkyl, aryl, aralkyl or alkylaryl and A is the monovalent steroid group of formula:

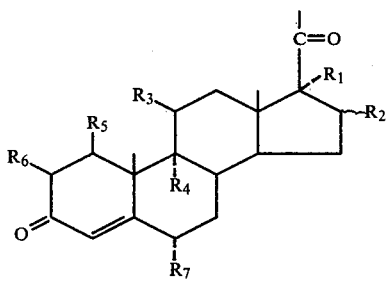

by sulphonating an alcohol of formula A—CH$_2$OH with a sulphonating agent of formula (R$_8$SO$_2$)$_n$—Y in which R$_8$ is a monovalent saturated hydrocarbon group and Y is oxygen when n is equal to 2, but is a halogen when n is equal to 1, in a dissolving or suspending medium in the presence of a stoichiometric excess of an amine in order to obtain a sulphonate of formula

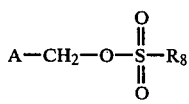

which is isolated and which is then thiocarboxylated by reaction in a solvent such as acetone with a thiocarboxylate of formula: M—S—CO—R in which M is an alkali metal or a monovalent lower trialkylamine group.

The yields are often mediocre. The periods of synthesis comprising the times of reaction and of isolation of the intermediate sulphonate and of the thioester produced are at least 30 hours.

The invention overcomes these disadvantages by enabling yields above 80% and currently reaching 90% to be obtained in total periods of synthesis of the order sometimes of 5 hours and of 3 to 4 hours only.

The applicants have, in fact, had the idea of eliminating the step of isolation of the intermediate sulphonate by effecting the two reactions of sulphonation and of thiocarboxylation in the same medium or solvent. However, they were confronted with unexpected difficulties both in the choice of solvent and in the reaction conditions. It appears, in fact, that interesting results giving a satisfactory yield and purity of the product are obtained only if the solvent is acetone or dimethylformamide. Solvents of very similar nature such as e.g. methylethyl ketone do not give suitable results. Moreover, said results are dependent on unexpected conditions relating to the sulphonating agent and to the acid binding agent. The sulphonating agent must be aliphatic and the acid binding agent must be a lower trialkylamine. For reasons which are not explained the use of heterocyclic compounds such as pyridine, albeit conventional in the prior art, or of aromatic compounds such as the tosylates, also conventional, in a solvent medium of acetone or dimethylformamide prevents the smooth progress of synthesis and even inhibts the sulphonation reaction.

The object of the invention is therefore a process for the preparation of a steroid of formula A—CH$_2$—S—COR in which R is alkyl, cycloalkyl, aryl, aralkyl or alkylaryl and A is the monovalent steroid group of formula:

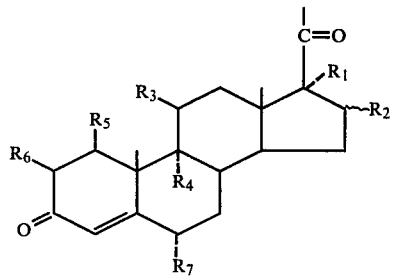

in which:
R$_1$ is hydrogen or hydroxy,
R$_2$ is hydrogen or an α-methyl or β-methyl group,
R$_3$ is hydroxy or oxo
R$_4$ is hydrogen or fluorine,
R$_5$ and R$_6$ are each hydrogen or together form a double bond between the carbon atoms carrying them,
R$_7$ is hydrogen or fluorine, whereby an alcohol of formula A—CH$_2$OH is sulphonated with a sulphonating agent of formula (R$_8$SO$_2$)$_n$—Y in which R$_8$ is a monovalent saturated hydrocarbon group and Y is oxygen when n is equal to 2, but a halogen when n is equal to 1 in a dissolving or suspending medium in the presence of a stoichiometric excess of an amine in order to obtain a sulphonate of formula

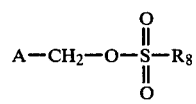

which is thiocarboxylated by reaction with a solution in acetone or in dimethylformamide of a thiocarboxylate of formula M—S—CO—R in which M is an alkali metal or a trialkylamine group, characterized in that it consists in effecting the sulphonation in the same medium as that used for the thiocarboxylation with a sulphonating agent whose group R$_8$ is aliphatic and in the presence of a lower trialkylamine as acid binding agent and in effecting the thiocarboxylation by bringing the solution or suspension of intermediate sulphonate directly in contact with the solution of thiocarboxylate without intermediate isolation of the sulphonate.

The expression "alkyl group" includes in particular groups from C$_1$ to C$_9$, both straight and branched, such as methyl, ethyl, propyl, t-butyl, pentyl, hexyl, heptyl, octyl and nonyl groups; the expression "cycloalkyl" includes in particular monovalent saturated cyclic C$_3$ to C$_7$ groups such as cyclopropyl, cyclobutyl, cyclohexyl and cycloheptyl groups; the expression "aryl" includes monocyclic carbocyclic aromatic groups which may optionally be substituted by halogen atoms, lower alkyl or alkoxy groups (C$_1$ to C$_6$). These aromatic groups may for example be phenyl, ethoxyphenyl, chlorophenyl, fluorophenyl, the substituents on the phenyl nucleus being in the ortho, meta or para position, while the expressions "alkylaryl" and "aralkyl" can have meanings corresponding to the preceding definitions given for the expressions "alkyl" and "aryl".

In the process according to the invention an alcohol of formula A—CH$_2$OH is first sulphonated with a sulphonating agent (R$_8$SO$_2$)$_n$—Y. It is necessary for R$_8$ to be aliphatic. R$_8$ may particularly be a straight or branched lower alkyl (C$_1$ to C$_{12}$) and especially methyl, ethyl, propyl, isopropyl, butyl, pentyl. When Y is halogen, it is preferably chlorine or bromine. The most usual sulphonating agent is methane sulphonylchloride.

The sulphonation is effected by applying a stoichiometric excess of the sulphonating agent in relation to the alcohol, e.g. 1.1 to 3 moles, preferably 1.25 to 1.75 moles, of sulphonating agent for 1 mole of the alcohol, working in a suspending or dissolving agent. This agent is acetone or dimethylformamide which is used in excess, for example in an amount of 3 to 15 liters per mole of alcohol used.

There are added to the reaction medium in suspension 1 to 5 moles, preferably 2.5 to 3.5 moles of a lower trialkylamine serving as acid binding agent per mole of alcohol. Each alkyl portion of this amine has 1 to 9 carbon atoms, preferably 2 to 6 carbon atoms. This may in particular be triethylamine or tributylamine, trimethylamine being less recommended. It has been established that the cycloalkyl, normal alkyl and heterocyclic amines, e.g. pyridine, are not suitable in practice, since the final yields obtained, if the reaction takes place, are limited and do not reach the high values which are sought.

The first step of sulphonation is effected preferably between −5° and +10° C. for 5 minutes to 1½ hours by adding the sulphonating agent to the suspension containing the alcohol, the acid binding agent and the acetone or dimethylformamide and by stirring for the entire reaction time, including during introduction of the sulphonating agent. There is obtained, if necessary after filtration of insoluble products, a solution of steroid alkylsulphonate in the acetone or dimethylformamide.

To effect the thiocarboxylation step, the solution obtained in the preceding step is used directly without intermediate isolation of the sulphonate obtained. For this purpose, a thiocarboxylate of alkali metal or of trialkylamine can be formed by reaction in ketonic medium or in a dimethylformamide medium, depending on whether one or other of these media has been chosen to effect the preceding sulphonation step, of a thiocarboxylic acid or anhydride with an alcoholate of alkali metal or of trialkylamine, each alkyl part of this amine having 1 to 6 carbon atoms, preferably 1 to 4 carbon atoms.

The thiocarboxylate obtained conforms to the formula: M—S—CO—R in which M is the alkali metal, particularly sodium and potassium, or the group derived from the trialkylamine.

The thio-acids used to prepare the thiocarboxylates may be aliphatic acids containing 2 to 10 carbon atoms whose chain may be straight or branched or they may be aromatic acids.

More especially, these acids may be thioacetic, thiopropionic, thiobutyric, thioisobutyric, thiopivalic, dimethyl-3,3-butanethioic, heptanethioic, decanethioic acid as well as pentanethioic, methyl-2-butanethioic, methyl-3-butanethioic, hexanethioic, methyl-4-pentanethioic, ethyl-2-butanethioic, octanethioic, ethyl-2-hexanethioic and nonanethioic acid. The aromatic acids are more especially thiobenzoic acid and p-fluoro- or p-chloro-thiobenzoic acids.

The quantity of acetone or of dimethylformamide is generally 1.3 to 10 liters, preferably 1.5 to 5 liters, ideally 1.5 to 2 liters per mole of thio-acid.

In general, the thio-acid is dissolved in the solvent and the solution obtained is then cooled below 5° C., e.g. to about 0° C., before the alcoholate is added, over a few minutes, for example 5 to 30 minutes, in a stoichiometric quantity. The solution is maintained at this temperature for half an hour to 2 hours. This separate preparation of the thiocarboxylate may be effected at the same time as the sulphonation is effected and therefore does not increase the total period of synthesis.

Subsequently, the solutions or the solution and the suspension in acetone or dimethylformamide obtained respectively from the sulphonation step of preparation of a thiocarboxylate are combined, for example by pouring the thiocarboxylate in solution over 5 to 30 minutes into the sulphonate in solution or in suspension.

The combined solutions are brought over 1 to 3 hours above 15° C., particularly to about 20° to 25° C., whereupon precipitation is effected by the addition of water and the thioester thus prepared is isolated in a conventional way.

The isolated products are generally of a very satisfactory purity; in the majority of cases a single crystallization in a suitable solvent enables a product of a purity suitable for therapeutic use to be obtained.

The following Examples illustrate the process according to the invention.

EXAMPLE 1

Step 1

500 grams (1.385 moles) of 11β, 17, 21-trihydroxy-pregn-4-ene-3,20-dione are suspended in 3.75 liters of acetone and 421 grams (4.150 moles) of triethylamine are then added.

The mixture is cooled to 0° C. and there are added with stirring at a temperature between 0° and 5° C. over about 1 hour 238 grams (2.075 moles) of methanesulphonylchloride in solution in 1.25 liters of acetone.

Stirring is subsequently maintained for 45 minutes and the reaction suspension is then filtered. The insoluble product washed with 0.5 liters of acetone is eliminated; the straw-yellow acetonic solution containing the 21-methane sulphonate of 11β,17-dihydroxyl-pregn-4-ene-3,20-dione is used as such in the following step.

Step 2

Separately and in parallel with step 1, 2.5 liters of acetone and then 196 grams (1.66 moles) of thiopivalic acid are introduced in a suitable reactor.

The solution is cooled to 0° C. and 89.5 grams (1.66 moles) of sodium methylate are then introduced in about 15 minutes, maintaining a temperature below 5° C.

It is maintained at this temperature for 1 hour and the acetonic solution obtained in the preceding step is then introduced over about 15 minutes.

The reaction medium is subsequently brought progressively to 20° C. over about 30 minutes and maintained at this temperature for 1 hour. 1 liter of demineralized water is then added to the suspension and the insoluble product is quickly dissolved, whereupon 4.4 liters of demineralized water are again added over about 30 minutes to precipitate the crude product.

Stirring is maintained for 30 minutes and the 21-thiopivalate of 11β,17-dihydroxy-pregn-4-ene-3,20-dione is filtered and washed with water.

After drying in vacuo at 50° C., 525 grams (yield=82.3%) of product are obtained which is crystallized in boiling absolute ethanol to give after drying 490 grams (final yield=77%), m.p.=225° C., of product whose analytical standards meet the requirements of therapeutic use. The synthesis has lasted 5 to 6 hours.

Example 2

Step 1

100 grams (0.254 moles) of 9α-fluoro-16α-methyl-11β, 17,21-trihydroxy-pregna-1,4-diene-3,20-dione and 77.1 grams (0.762 moles) of triethylamine are suspended in 0.75 liters of acetone. The suspension is cooled to 0° C. and there are added over about 10 minutes at a temperature between 0° and +5° C. 66.2 grams (0.380 moles) of methanesulphonic anhydride in solution in 0.25 liters of acetone.

A solution is obtained which is stirred at about 0° C. for 45 minutes.

The pale yellow solution containing the 21-methanesulphonate of 11β,17-dihydroxy-9α-fluoro-16α-methyl-pregna-1,4-diene-3,20-dione is used as such in the following step.

Step 2

In parallel with the preceding step, 0.5 liters of acetone and 43.75 grams (0.280 moles) of p-fluorothio-benzoic acid are introduced in a suitable reactor. After cooling to 0° C. there are introduced over about 15 minutes into the solution 15.15 grams (0.280 moles) of sodium methylate, maintaining the temperature below 5° C. The reaction mixture is stirred for about 30 minutes at 5° C. and the acetonic solution obtained in the preceding step is then introduced over about 15 minutes.

The solution is brought progressively to 20° C. over about 30 minutes and maintained at this temperature for 45 minutes.

0.2 liters of demineralized water are subsequently addded rapidly to dissolve the precipitate and a new quantity of 0.9 liters of demineralized water is then added over about 30 minutes to precipitate the crude product. After precipitation, stirring is maintained for 30 minutes and the insoluble product is filtered and washed with water. After drying in vacuo at 50° C. there are obtained 124 grams (yield=92%) of crude 21-p-fluorothiobenzoate of 11β,17-dihydroxy-9α-fluoro-16α-methyl-pregna-1,4-diene-3,20-dione. Synthesis has lasted about 4¼ hours.

This product crystallized in boiling absolute ethanol gives 105.4 grams (final yield=78.2%), m.p.=208° C., of product suitable for therapeutic use.

EXAMPLES 3 TO 42

Proceeding as in Examples 1 or 2 with other 21-hydroxy steroids and thio-acids, the thioesters listed in Table I below were obtained.

TABLE I

| Ex. | Thioacid | Starting steroid | Product obtained | Yield % | Time of synthesis | M.p. |
|---|---|---|---|---|---|---|
| 3 | Thioacetic acid | 11β,17,21-trihydroxy-pregn-4-ene-3,20-dione | 21-thioacetate of 11β,17-dihydroxy-pregn-4-ene-3,20-dione | 93 | 4 h 30 | 212° C. |
| 4 | Thiopropionic acid | 11β,17,21-trihydroxy-pregn-4-ene-3,20-dione | 21-thiopropionate of 11β,17-dihydroxy-pregn-4-ene-3,20-dione | 86 | 4 h 30 | 213° C. |
| 5 | Thiobutyric acid | 11β,17,21-trihydroxy-pregn-4-ene-3,20-dione | 21-thiobutyrate of 11β,17-dihydroxy-pregn-4-ene-3,20-dione | 84 | 4 h | 194° C. |
| 6 | Thioisobutyric acid | | 21-thioisobutyrate of 11β,17-dihydroxy-pregn-4-ene-3,20-dione | 84 | 4 h 30 | 199° C. |
| 7 | Dimethyl-3,3 butanethioic acid | 11β,17,21-trihydroxy-pregn-4-ene-3,20-dione | 21-(3,3-dimethylbutane-thioate) of 11β,17-dihydroxy-pregn-4-ene-3,20-dione | 90 | 5 h | 216° |
| 8 | Heptanethioic acid | | 21-heptanethioate of 11β,17-dihydroxy-pregn-4-ene-3,20-dione | 82 | 5 h 30 | 121° C. |
| 9 | Decanethioic acid | 11β,17,21-trihydroxy-pregn-4-ene-3,20-dione | 21-decanethioate of 11β,17-dihydroxy-pregn-4-ene-3,20-dione | 81 | 5 h 30 | 137° C. |
| 10 | Fluoro-thio-benzoic acid | 11β,17,21-trihydroxy-pregn-4-ene-3,20-dione | 21-(p-fluorothiobenzoate) of 11β,17-dihydroxy-pregn-4-ene-3,20-dione | 72 | 6 h 30 | 230° C. |
| 11 | Thioacetic acid | 17,21-dihydroxy-pregn-4-ene-3,11,20-trione | 21-thioacetate of 17-hydroxy-pregn-4-ene-3,11,20-trione | 93 | 4 h | 224° C. |
| 12 | Thioproprionic acid | 17,21-dihydroxy-pregn-4-ene-3,11,20-trione | 21-thiopropionate of 17-hydroxy-pregn-4-ene-3,11,20-trione | 85 | 4 h | 201° C. |
| 13 | Thiobutyric acid | 17,21-dihydroxy-pregn-4-ene-3,11,20-trione | 21-thiobutyrate of 17-hydroxy-pregn-4-ene-3,11,20-trione | 93 | 4 h | 155° C. |
| 14 | Thioisobutyric acid | 17,21-dihydroxy-pregn-4-ene-3,11,20-trione | 21-thioisobutyrate of 17-hydroxy-pregn-4-ene-3,11,20-trione | 87 | 4 h | 188° C. |
| 15 | Thiopivalic acid | 17,21-dihydroxy-pregn-4-ene-3,11,20-trione | 21-thiopivalate of 17-hydroxy-pregn-4-ene-3,11,20-trione | 82 | 4 h 30 | 277° C. |

TABLE I-continued

| Ex. | Thioacid | Starting steroid | Product obtained | Yield % | Time of synthesis | M.p. |
|---|---|---|---|---|---|---|
| 16 | Heptanethioic acid | 17,21-dihydroxy-pregn-4-ene-3,11,20-trione | 21-heptanethioate of 17-hydroxy-pregn-4-ene-3,11,20-trione | 80 | 5 h | 126° C. |
| 17 | Decanethioic acid | 17,21-dihydroxy-pregn-4-ene-3,11,20-trione | 21-decanethioate of 17-hydroxy-pregn-4-ene-3,11,20-trione | 78 | 5 h 30 | 115° C. |
| 18 | Fluoro-thio-benzoic acid | 17,21-dihydroxy-pregn-4-ene-3,11,20-trione | 21-(p-fluorothiobenzoate) of 17-hydroxy-pregn-4-ene-3,11,20-trione | 82 | 6 h 30 | 167° C. |
| 19 | Thioacetic acid | 11$\beta$,17,21-trihydroxy-pregna-1,4-diene-3,20-dione | 21-thioacetate of 11$\beta$,17-dihydroxy-pregna-1,4-diene-3,20-dione | 84 | 4 h 30 | 244° C. |
| 20 | Thiopropionic acid | 11$\beta$,17,21-trihydroxy-pregna-1,4-diene-3,20-dione | 21-thiopropionate of 11$\beta$,17-dihydroxy-pregna-1,4-diene-3,20-dione | 85 | 4 h | 240° C. |
| 21 | Thiobutyric acid | 11$\beta$,17,21-trihydroxy-pregna-1,4-diene-3,20-dione | 21-thiobutyrate of 11$\beta$,17-dihydroxy-pregna-1,4-diene-3,20-dione | 79 | 5 h | 211° C. |
| 22 | Thioisobutyric acid | 11$\beta$,17,21-trihydroxy-pregna-1,4-diene-3,20-dione | 21-thioisobutyrate of 11$\beta$,17-dihydroxy-pregna-1,4-diene-3,20-dione | 92 | 5 h | 200° C. |
| 23 | Thiopivalic acid | 11$\beta$,17,21-trihydroxy-pregna-1,4-diene-3,20-dione | 21-thiopivalate of 11$\beta$,17-dihydroxy-pregna-1,4-diene-3,20-dione | 85 | 4 h | 239° C. |
| 24 | Heptanethioic acid | 11$\beta$,17,21-trihydroxy-pregna-1,4-diene-3,20-dione | 21-heptanethioate of 11$\beta$,17-dihydroxy-pregna-1,4-diene-3,20-dione | 82 | 4 h 30 | 160° C. |
| 25 | Decanethioic acid | 11$\beta$,17,21-trihydroxy-pregna-1,4-diene-3,20-dione | 21-decanethioate of 11$\beta$,17-dihydroxy-pregna-1,4-diene-3,20-dione | 75 | 5 h | 162° C. |
| 26 | Fluoro-thio-benzoic acid | 11$\beta$,17,21-trihydroxy-pregna-1,4-diene-3,20-dione | 21-(p-fluorothiobenzoate) of 11$\beta$,17-dihydroxy-pregna-1,4-diene-3,20-dione | 72 | 6 h | 242° C. |
| 27 | Thioacetic acid | 17,21-dihydroxy-pregna-1,4-diene-3,11,20-trione | 21-thioacetate of 17-hydroxy-pregna-1,4-diene-3,11,20-trione | 85 | 4 h | 233° C. |
| 28 | Thiopropionic acid | 17,21-dihydroxy-pregna-1,4-diene-3,11,20-trione | 21-thiopropionate of 17-hydroxy-pregna-1,4-diene-3,11,20-trione | 91 | 4 h | 217° C. |
| 29 | Thiobutyric acid | 17,21-dihydroxy-pregna-1,4-diene-3,11,20-trione | 21-thiobutyrate of 17-hydroxy-pregna-1,4-diene-3,11,20-trione | 89 | 4 h | 175° C. |
| 30 | Thioisobutyric acid | 17,21-dihydroxy-pregna-1,4-diene-3,11,20-trione | 21-thioisobutyrate of 17-hydroxy-pregna-1,4-diene-3,11,20-trione | 88 | 4 h | 207° C. |
| 31 | Thiopivalic acid | 17,21-dihydroxy-pregna-1,4-diene-3,11,20-trione | 21-thiopivalate of 17-hydroxy-pregna-1,4-diene-3,11,20-trione | 86 | 4 h | 253° C. |
| 32 | Heptanethioic acid | 17,21-dihydroxy-pregna-1,4-diene-3,11,20-trione | 21-heptanethioate of 17-hydroxy-pregna-1,4-diene-3,11,20-trione | 82 | 5 h | 151° C. |
| 33 | Decanethioic acid | 17,21-dihydroxy-pregna-1,4-diene-3,11,20-trione | 21-decanethioate of 17-hydroxy-pregna-1,4-diene-3,11,20-trione | 77 | 6 h | 108° C. |
| 34 | Fluorothio-benzoic acid | 17,21-dihydroxy-pregna-1,4-diene-3,11,20-trione | 21-(p-fluorothiobenzoate) of 17-hydroxy-pregna-1,4-diene-3,11,20-trione | 82 | 5 h 30 | 186° C. |
| 35 | Thioacetic acid | 9-fluoro-16$\alpha$-methyl-11$\beta$,17,21-trihydroxy-pregna-1,4-diene-3,20 dione | 21-thioacetate of 11$\beta$,17-dihydroxy-9-fluoro-16$\alpha$-methyl-pregna-1,4-diene-3,20-dione | 86 | 4 h | 231° C. |
| 36 | Thiopropionic acid | 9-fluoro-16$\alpha$-methyl-11$\beta$,17,21-trihydroxy-pregna-1,4-diene-3,20 dione | 21-thiopropionate of 11$\beta$,17-dihydroxy-9-fluoro-16$\alpha$-methyl-pregna-1,4-diene-3,20-dione | 78 | 4 h | 188° C. |
| 37 | Thiobutyric acid | 9-fluoro-16$\alpha$-methyl-11$\beta$,17,21-trihydroxy-pregna-1,4-diene-3,20 dione | 21-thiobutyrate of 11$\beta$,17-dihydroxy-9-fluoro-16$\alpha$-methyl-pregna-1,4-diene-3,20-dione | 82 | 4 h | 182° C. |
| 38 | Thioisobutyric acid | 9-fluoro-16$\alpha$-methyl-11$\beta$,17,21-trihydroxy-pregna-1,4-diene-3,20 dione | 21-thioisobutyrate of 11$\beta$,17-dihydroxy-9-fluoro-16$\alpha$-methyl-pregna-1,4-diene-3,20-dione | 82 | 4 h | 213° C. |
| 39 | Thiopivalic acid | 9-fluoro-16$\alpha$-methyl-11$\beta$,17,21-trihydroxy-pregna-1,4-diene-3,20 dione | 21-thiopivalate of 11$\beta$,17-dihydroxy-9-fluoro-16$\alpha$-methyl-pregna-1,4-diene-3,20-dione | 90 | 5 h | 245° C. |
| 40 | Heptanethioic acid | 9-fluoro-16$\alpha$-methyl-11$\beta$,17,21-trihydroxy-pregna- | 21-heptanethioate of 11$\beta$,17-dihydroxy-9- | 84 | 6 h | 180° C. |

TABLE I-continued

| Ex. | Thioacid | Starting steroid | Product obtained | Yield % | Time of synthesis | M.p. |
|---|---|---|---|---|---|---|
| 41 | Decanethioic acid | 9-fluoro-16α-methyl-11β,17,21-trihydroxy-pregna-1,4-diene-3,20 dione | 21-decanethioate of 11β,17-dihydroxy-9-fluoro-16α-methyl-pregna-1,4-diene-3,20,dione | 78 | 5 h 30 | 147° C. |
| 42 | Thioacetic acid | 6α,9α-difluoro-16α-methyl-11β,17α,21-trihydroxy-pregna-1,4-diene-3,20-dione | 21-thioacetate of 11β,17α-dihydroxy-6α,9α-difluoro-16α-methyl-pregna-1,4-diene-3,20-dione | 94 | 4 h | 238° |
| 43 | Thiopropionic acid | 6α,9α-difluoro-16α-methyl-11β,17α,21-trihydroxy-pregna-1,4-diene-3,20-dione | 21-thiopropionate of 11β,17α-dihydroxy-6α,9α-difluoro-16α-methyl-pregna-1,4-diene-3,20 dione | 85 | 4 h | 240° C. |

(first row continuation: 1,4-diene-3,20 dione → fluoro-16α-methyl-pregna-1,4-diene-3,20-dione)

EXAMPLES 44 TO 86

Examples 1 to 43 are repeated, but replacing acetone by the same volume of dimethylformamide. Results similar to those gained in Examples 1 to 43 are obtained.

COMPARATIVE EXAMPLE 1

Example 1 is repeated, but replacing the triethylamine serving as acid binding agent by an equivalent molar quantity of other amines listed in Table II below, which likewise gives the yields obtained. The synthesis cannot be effected in a pyridine medium. The yield is very low in a cyclohexylamine medium. n-Butylamine gives a yield four times less than the trialkylamines prescribed according to the invention.

TABLE II

| Amine | Yield |
|---|---|
| pyridine | 0% |
| cyclohexylamine | 15% |
| n-butylamine | 20% |
| tributylamine | 75% |
| triethylamine | 78% |

This Example shows that the choice of the acid binding agent is decisive for the process of the invention, whereas importance has never been attributed to this choice in the prior processes not working in an acetone or dimethylformamide medium.

COMPARATIVE EXAMPLE 2

Example 1 is repeated, but replacing the acetone by an equivalent volume of the media listed in Table III, which likewise gives the yields and impurities.

The yield with methylisobutyl acetone, though closely akin to acetone, is only 39%. With methylethyl ketone the yield is 70%; in addition to this already notable difference in yield of 7% (that is 10% in relative value), the thioester obtained is much more impure and the subsequent purification steps which it requires lower the yield very clearly and increase the industrial synthesis time.

TABLE III

| Solvent | Yield | Positive polar impurities | Negative polar impurities |
|---|---|---|---|
| Acetonitrile | 54% | 3− +,++,+ | 2− ±, ++ |
| HMPT (hexamethylphosphoro)triamide | 60% | 5− +,+,+,+,+ | 1 ± |
| DMSO (dimethylsulphoxide) | 55% | 4− +,+,+,+ | 1− ++ |
| MEK (methylethyl ketone) | 70% | 3− +,±,+, | 1− ++ |
| MIBK (methylisobutyl ketone) | 39% | 4− +,+,+,++ | 1− ++ |
| DMF or acetone (dimethylformamide) according to the invention | 77% | 1− ± | 1− + |

The polarity of the impurities is expressed by their Rf in thin-layer chromatography in relation to the JO 1016 in the 7/3 benzene-acetone elution solvent. Their approximate magnitude is proportional to the number of +.

COMPARATIVE EXAMPLE 3

Example 1 is repeated, but replacing the methane sulphonylchloride by an equal molar quantity of p-toluene-sulphonylchloride.

The sulphonation reaction does not take place.

EXAMPLE 87

Step 1

100 grams (0.277 moles) of 11β,17α,21-trihydroxy-pregn-4-ene-3,20-dione are solubilised in 0.75 liters of dimethylformamide (DMF). 84.2 grams of triethylamine (0.830 moles) are subsequently added.

At a temperature near 0° C. 47.6 g (0.415 moles) of methanesulphonylchloride are added in solution in 0.25 liters of DMF over 30 minutes. After introduction, the mixture is stirred at 0° C. for 1 hour.

The insoluble product is filtered and washed with a minimum of DMF. The solution of an orange color which is obtained is used as such in the following step.

Step 2

As described in Example 1, but using DMF as reaction solvent, sodium thiopivalate is prepared from 39.2 grams of thiopivalic acid and 17.9 grams of sodium methylate in 0.5 liters of DMF.

The orange solution obtained in the preceding step is introduced into the solution of the sodium salt.

The mixture is stirred for 45 minutes at 20° C. and 1.4 liters of demineralized water are then introduced over 30 minutes to precipitate the product. Stirring is maintained for 30 minutes and the product is filtered and washed with water.

After drying in vacuo at 50° C. there are obtained 115 grams of 21-thiopivalate of 11β,17α-dihydroxy-pregn-4-ene-3,20-dione (yield=90.1%). The product is crystallized in ethanol as in Example 1.

We claim:

1. In a process for the preparation of a steriod of formula A—CH$_2$—S—COR in which R is alkyl, cycloalkyl, aryl, aralkyl or alkylaryl and A is the monovalent steriod group of formula:

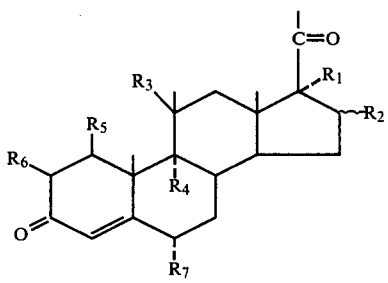

in which:

R$_1$ is hydrogen or hydroxy,

R$_2$ is hydrogen or an α-methyl or β-methyl group,

R$_3$ is hydroxy or oxo

R$_4$ is hydrogen or fluorine,

R$_5$ and R$_6$ are each hydrogen or together form a double bond between the carbon atoms carrying them, R$_7$ is hydrogen or fluorine, whereby an alcohol of formula A—CH$_2$OH is sulphonated with a sulphonating agent of formula (R$_8$SO$_2$)$_n$—Y in which R$_8$ is a monovalent saturated hydrocarbon group and Y is oxygen when n is equal to 2, but is a halogen when n is equal to 1 in a dissolving or suspending medium in the presence of a stoichiometric excess of an amine to obtain a sulphonate of formula:

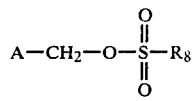

which is thiocarboxylated by a reaction with a solution in acetone or in dimethylformamide of a thiocarboxylate of formula M—S—CO—R in which M is an alkali metal or a trialkylamine group, the improvement which consists in effecting the sulphonation in the same medium as that used for the thiocarboxylation with a sulphonating agent whose group R$_8$ is aliphatic and in the presence of a lower trialkylamine as acid binding agent and in effecting the thiocarboxylation by bringing the solution or suspension of intermediate suphonate directly in contact with the solution of thiocarboxylate without intermediate isolation of the sulphonate.

2. Process according to claim 1, which consists in using in the suphonating step 3 to 15 liters of suspending or dissolving medium per mole of alcohol used.

3. Process according to claim 1, wherein Y is oxygen, chlorine or bromine.

4. Process according to claim 1, wherein the sulphonating agent is employed at the rate of 1.1 to 3 moles per mole of alcohol.

5. Process according to claim 1, where in the acid binding agent is a trialkylamine having 2 to 6 carbon atoms.

6. Process according to claim 1, which consists in effecting the sulphonation in the presence of 1 to 5 moles of acid binding agent per mole of alcohol.

7. Process according to claim 1, which consists in effecting the sulphonation between −5° and +10° C. by constantly stirring the reaction medium for about 5 minutes to 1½ hours.

8. Process according to claim 1, which consists in using to prepare the solution of thiocarboxylate 1,3 to 10 liters of solvent per mole of thio-acid.

9. Process according to claim 1, wherein for thiocarboxylation the reaction medium is brought to between 20° and 25° C. for about 1 to 3 hours.

10. Process according to claim 1, wherein the sulphonating agent is employed at the rate of 1.25 to 1.75 moles per mole of alcohol.

* * * * *